United States Patent
Chen et al.

(10) Patent No.: US 10,096,712 B2
(45) Date of Patent: Oct. 9, 2018

(54) FINFET DEVICE AND METHOD OF FORMING AND MONITORING QUALITY OF THE SAME

(71) Applicant: TAIWAN SEMICONDUCTOR MANUFACTURING CO., LTD., Hsinchu (TW)

(72) Inventors: Chang-Yin Chen, Taipei (TW); Che-Cheng Chang, New Taipei (TW); Chih-Han Lin, Hsinchu (TW); Horng-Huei Tseng, Hsinchu (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 0 days.

(21) Appl. No.: 15/002,287

(22) Filed: Jan. 20, 2016

(65) Prior Publication Data

US 2017/0110567 A1   Apr. 20, 2017

Related U.S. Application Data

(60) Provisional application No. 62/244,087, filed on Oct. 20, 2015, provisional application No. 62/261,746, filed on Dec. 1, 2015.

(51) Int. Cl.
*H01L 21/82* (2006.01)
*H01L 29/78* (2006.01)
(Continued)

(52) U.S. Cl.
CPC ...... *H01L 29/785* (2013.01); *H01L 21/32136* (2013.01); *H01L 21/32137* (2013.01);
(Continued)

(58) Field of Classification Search
CPC ... H01L 29/785; H01L 29/517; H01L 29/518; H01L 29/0611
See application file for complete search history.

(56) References Cited

U.S. PATENT DOCUMENTS 9,620,417 B2   4/2017   Chen et al.
9,793,269 B2 * 10/2017   Chang ............... H01L 27/0886
(Continued)

FOREIGN PATENT DOCUMENTS

| DE | 102015105856 A1 | 3/2016 |
| DE | 102016100035 A1 | 1/2017 |
| KR | 1020050008687 A | 1/2005 |
| KR | 1020060060276 A | 6/2006 |
| KR | 1020090005122 A | 1/2009 |
| KR | 1020140111577 A | 9/2014 |

OTHER PUBLICATIONS

Pending U.S. Appl. No. 14/478,915, filed Sep. 5, 2014.

*Primary Examiner* — Benjamin Sandvik
(74) *Attorney, Agent, or Firm* — Slater Matsil, LLP

(57) ABSTRACT

A FinFET structure with a gate structure having two notch features therein and a method of forming the same is disclosed. The method includes the steps of: forming a plurality of fins supported by a substrate; depositing a gate layer on the fins; and etching the gate layer by plasma etching with an etching gas to form a gate having two notch features. The etching gas is supplied at a ratio of a flow rate at a center area of the substrate to a flow rate at a periphery area of the substrate in a range from 0.2 to 1. The disclosure also provides a method of monitoring a quality of the FinFET device, the method comprising: measuring a profile of the notch feature; and obtaining the quality of the FinFET device by comparing the profile of the notch feature with a predetermined criterion.

20 Claims, 15 Drawing Sheets

(51) Int. Cl.
*H01L 29/66* (2006.01)
*H01L 29/51* (2006.01)
*H01L 29/49* (2006.01)
*H01L 29/423* (2006.01)
*H01L 21/3213* (2006.01)
*H01L 21/66* (2006.01)
*H01L 21/8234* (2006.01)
*H01L 21/67* (2006.01)
*G01N 21/88* (2006.01)

(52) U.S. Cl.
CPC .. *H01L 21/32139* (2013.01); *H01L 21/67288* (2013.01); *H01L 21/823431* (2013.01); *H01L 21/823437* (2013.01); *H01L 22/12* (2013.01); *H01L 29/42372* (2013.01); *H01L 29/4916* (2013.01); *H01L 29/517* (2013.01); *H01L 29/518* (2013.01); *H01L 29/66795* (2013.01); *G01N 2021/8848* (2013.01)

(56) References Cited

U.S. PATENT DOCUMENTS

| | | |
|---|---|---|
| 2003/0197872 A1 | 10/2003 | Littau et al. |
| 2007/0229807 A1 | 10/2007 | Lally et al. |
| 2008/0311688 A1* | 12/2008 | Yamashita ........ G06F 17/5036 438/14 |
| 2013/0071957 A1* | 3/2013 | Wang .................... H01L 22/12 438/17 |
| 2014/0252486 A1 | 9/2014 | Lin et al. |
| 2015/0060957 A1* | 3/2015 | Lee ..................... H01L 29/8086 257/279 |
| 2015/0214368 A1* | 7/2015 | Chang ................ H01L 29/7851 257/190 |
| 2016/0043079 A1* | 2/2016 | Chang ................ H01L 27/0886 257/401 |
| 2017/0005005 A1 | 1/2017 | Chen et al. |

* cited by examiner

FINFET DEVICE AND METHOD OF FORMING AND MONITORING QUALITY OF THE SAME

PRIORITY CLAIM AND CROSS-REFERENCE

This application claims priorities to U.S. Application Ser. No. 62/244,087 and 62/261,746, filed Oct. 20, 2015 and Dec. 1, 2015 respectively, which are herein incorporated by reference.

BACKGROUND

Semiconductor devices are widely used in a large number of electronic devices, such as computers, cell phones, and others. Semiconductor devices comprise integrated circuits that are formed on semiconductor wafers by depositing many types of thin films of material over the semiconductor wafers, and patterning the thin films of material to form the integrated circuits.

To address the increase of manufacturing complexity and the accompanied problems in manufacturing process, advances in IC processing and manufacturing are necessary. For example, a three dimensional transistor, such as a fin-like field-effect transistor (Fin-FET), has been introduced to replace a planar transistor. In the manufacturing process of the Fin-FET devices, further improvements are constantly necessary to satisfy the performance requirement in the scaling down process.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
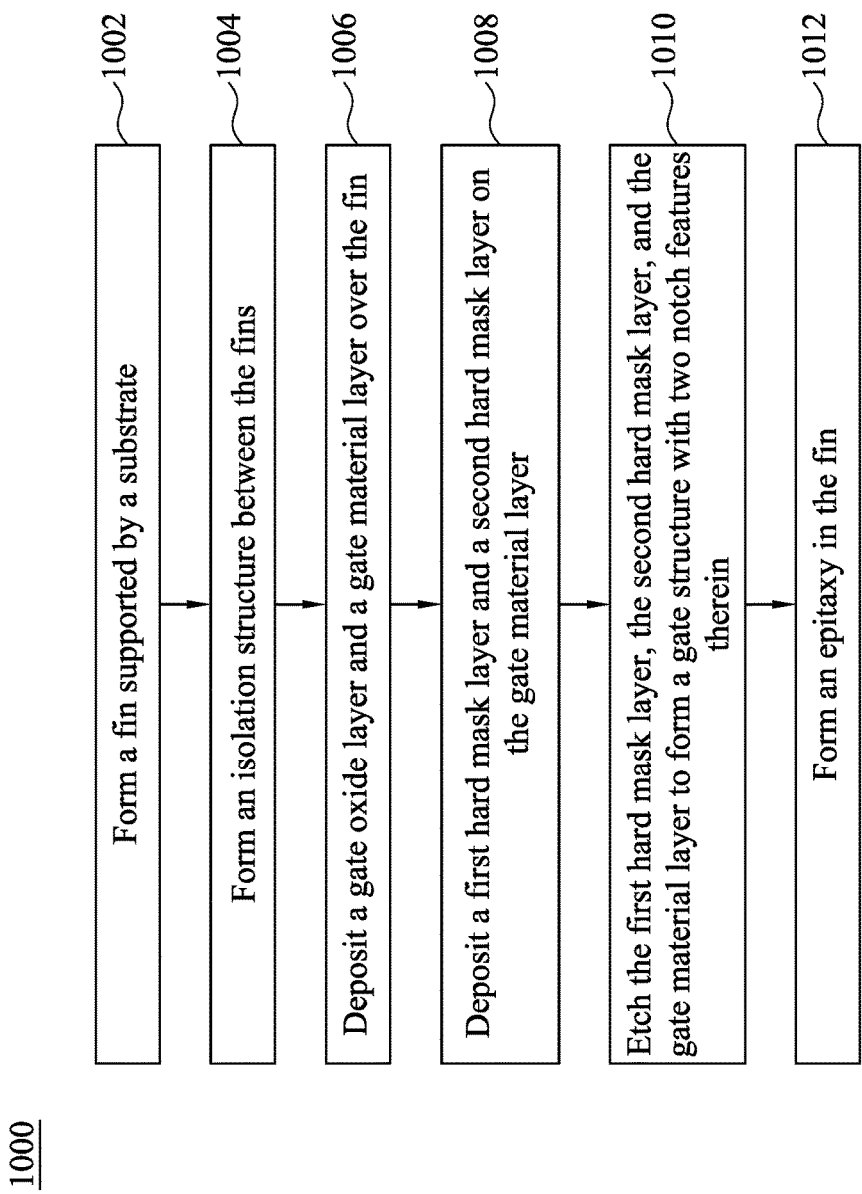
FIG. 1 illustrates an exemplary flow chart for manufacturing a FinFET device in accordance with the embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

The singular forms "a," "an" and "the" include plural referents unless the context clearly dictates otherwise. Therefore, reference to, for example, a conductive plug includes aspects having two or more such plug, unless the context clearly indicates otherwise. Further, spatially relative terms, such as "beneath," "below," "lower," "above," "upper" and the like, may be used herein for ease of description to describe one element or feature's relationship to another element(s) or feature(s) as illustrated in the figures.

In the manufacture of a semiconductor device, it is very important for an integrated circuit to operate in a stable condition, thus any possibility of causing short circuit should be avoided. In a fin field-effect transistor (FinFET), one of such short circuit may occur between a source/drain area in a fin structure and a gate structure wrapping the fin. In a normal situation, during forming the gate structure wrapping the fin structure, a removing process such as etching is controlled to remove a gate material layer to form a desired shape of the gate structure. However, in a traditional etching way to form the gate structure, the gate structure in a center area of a substrate and the gate structure in a periphery area of the substrate are under different etching rate. Such different etching rate may cause different profiles of gate structures in the periphery area with respect to the gate structures in the center area. For example, the gate structure in the periphery area may be under etched which may result in a footing feature (or a gate protrusion) extending from a lower portion of the gate structure. The footing feature may cause a short circuit between the gate structure and a source/drain area formed subsequently.

To solve the problem of short circuit between the gate structure and the source/drain area that is caused by the footing feature of the gate structure, a method is provided to make gate structures in both the center area and the periphery area have two notch features therein. In the disclosure, a different flow rate of etching gas at the center area compared to the periphery area during a dry plasma etching process is applied to improve the etching process (i.e. increasing etching rate) at the periphery area. In addition, by properly adjusting other etching parameters, such as etching pressure, RF bias voltage, and over etching time, gate structures in the center area and in the periphery area both have the two notch features with a same profile. In particular, the dimension (or a set of distances) of the notch features may be controlled in a predetermined criterion. Thus the FinFET device will have a good electrical property which can be measured from a wafer acceptance test (WAT) procedure.

Now referring to FIG. 1, which is an exemplary flow chart for manufacturing a FinFET device according to one embodiment of the present disclosure. The flow chart illustrates only a relevant part of the entire manufacturing process. It is understood that additional operations may be provided before, during, and after the operations shown by FIG. 1, and some of the operations described below can be replaced or eliminated for additional embodiments of the method. The order of the operations/processes may be interchangeable.

As shown in FIG. 1, an embodiment method 1000 of forming two notch features in a gate structure of a FinFET is provided. In step 1002, a fin supported by a substrate is formed. In step 1004, an isolation structure is formed between the fins. In step 1006, a gate oxide layer and a gate material layer are deposited over the fin. In step 1008, a first hard mask layer and a second hard mask layer are deposited on the gate material layer. In step 1010, the second hard mask layer, the second hard mask layer, and the gate material layer are etched to form a gate structure with two notch features therein. In step 1012, an epitaxy is formed in the fin.

Figure 2:
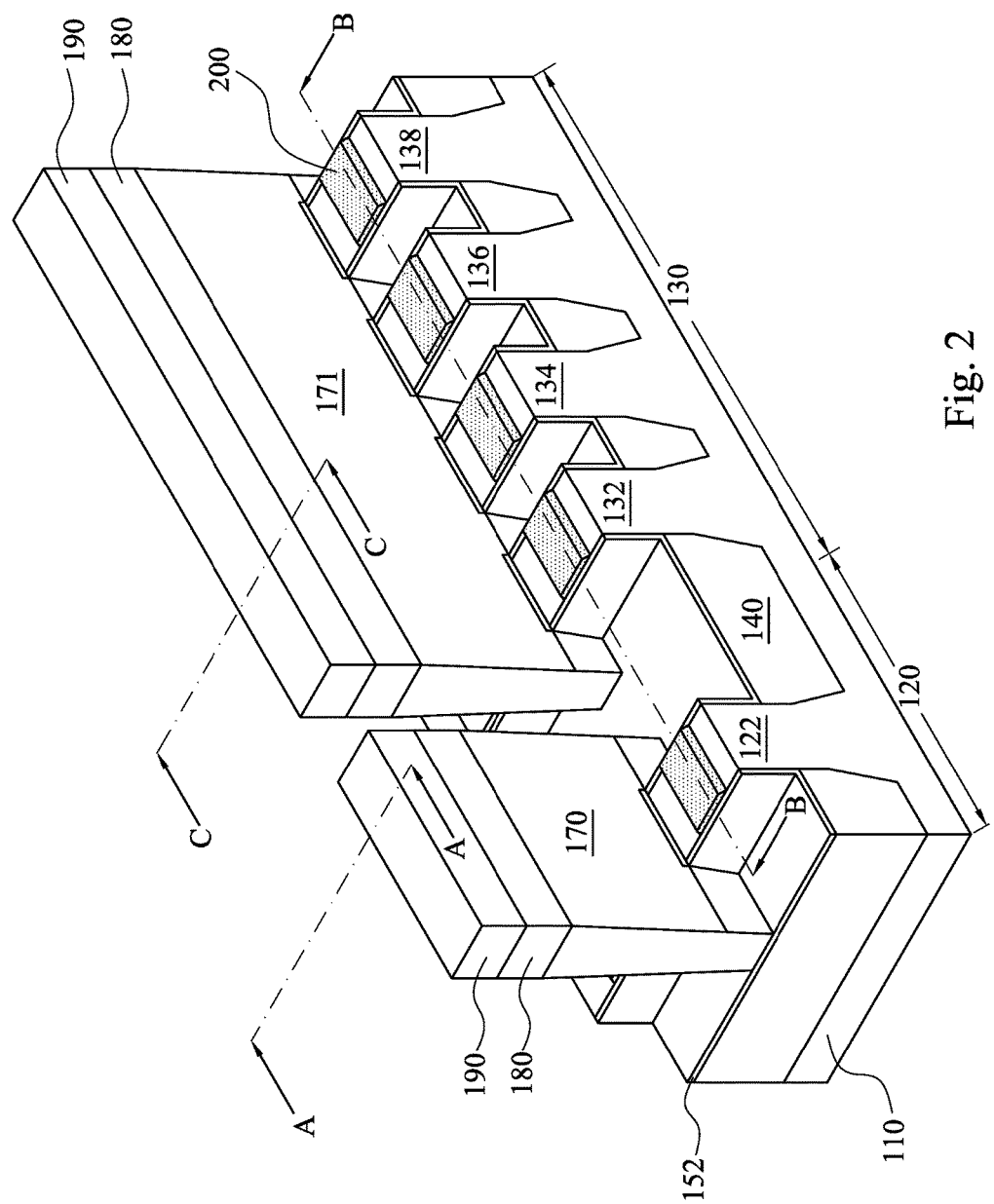
FIG. 2 illustrates a three dimensional view of a FinFET device in accordance with the embodiment.
Figure 3A:
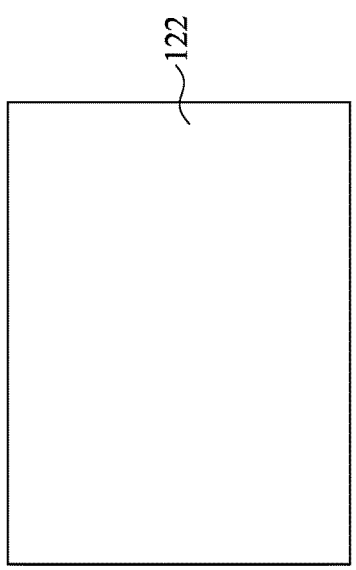
FIGS. 3A, 4A, 5A, 6A, and 7A illustrate various cross sectional views of a FinFET device along line A-A in FIG. 2 at different stages of manufacturing processes in accordance with the embodiments.
Figure 3B:
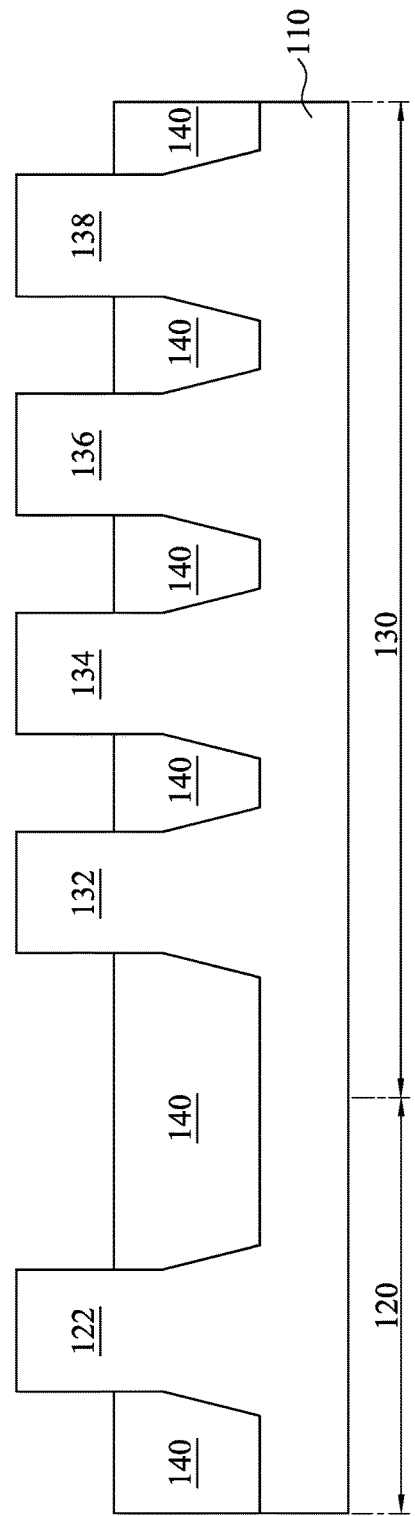
FIGS. 3B, 4B, 5B, 6B, and 7B illustrate various cross sectional views of a FinFET device along line B-B in FIG. 2 at different stages of manufacturing processes in accordance with the embodiments.
Figure 4A:
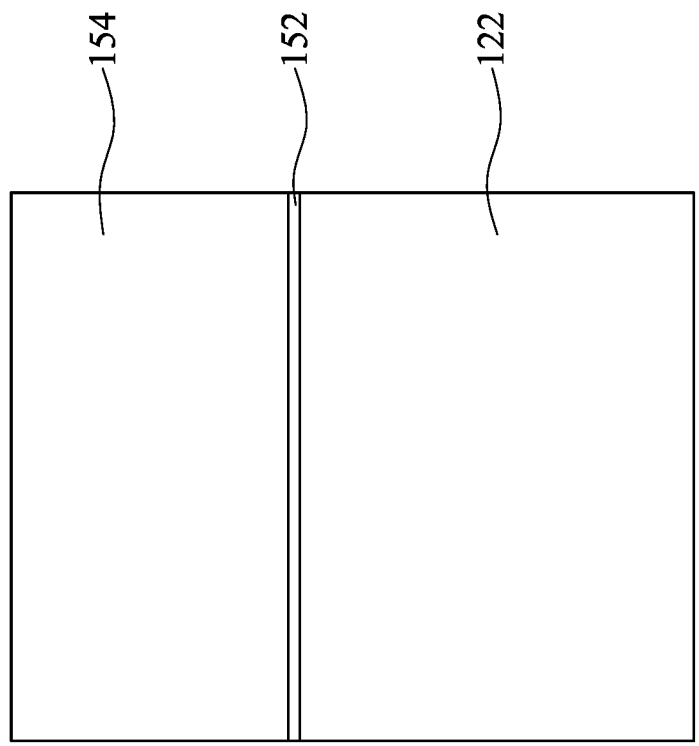
Figure 4B:
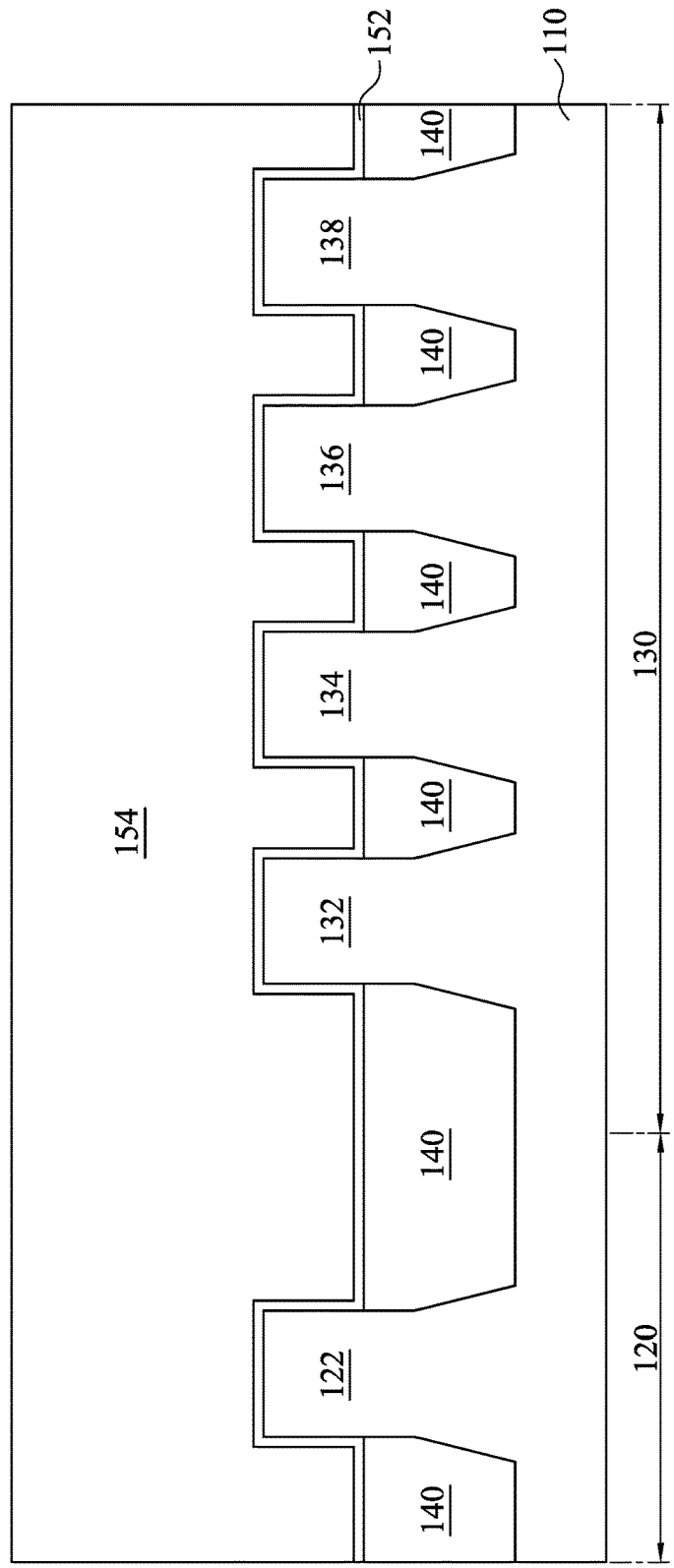
Figure 5A:
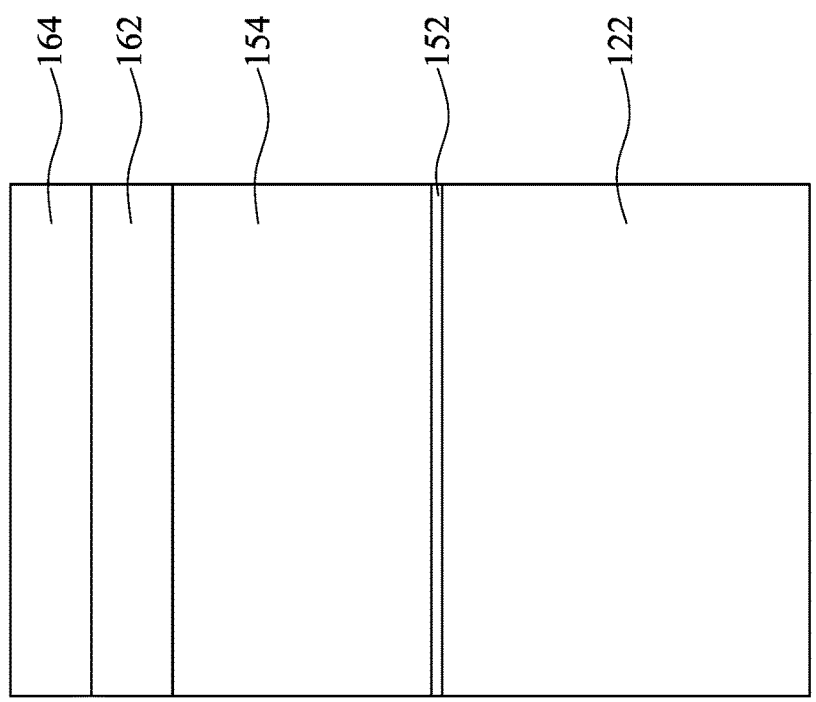
Figure 5B:
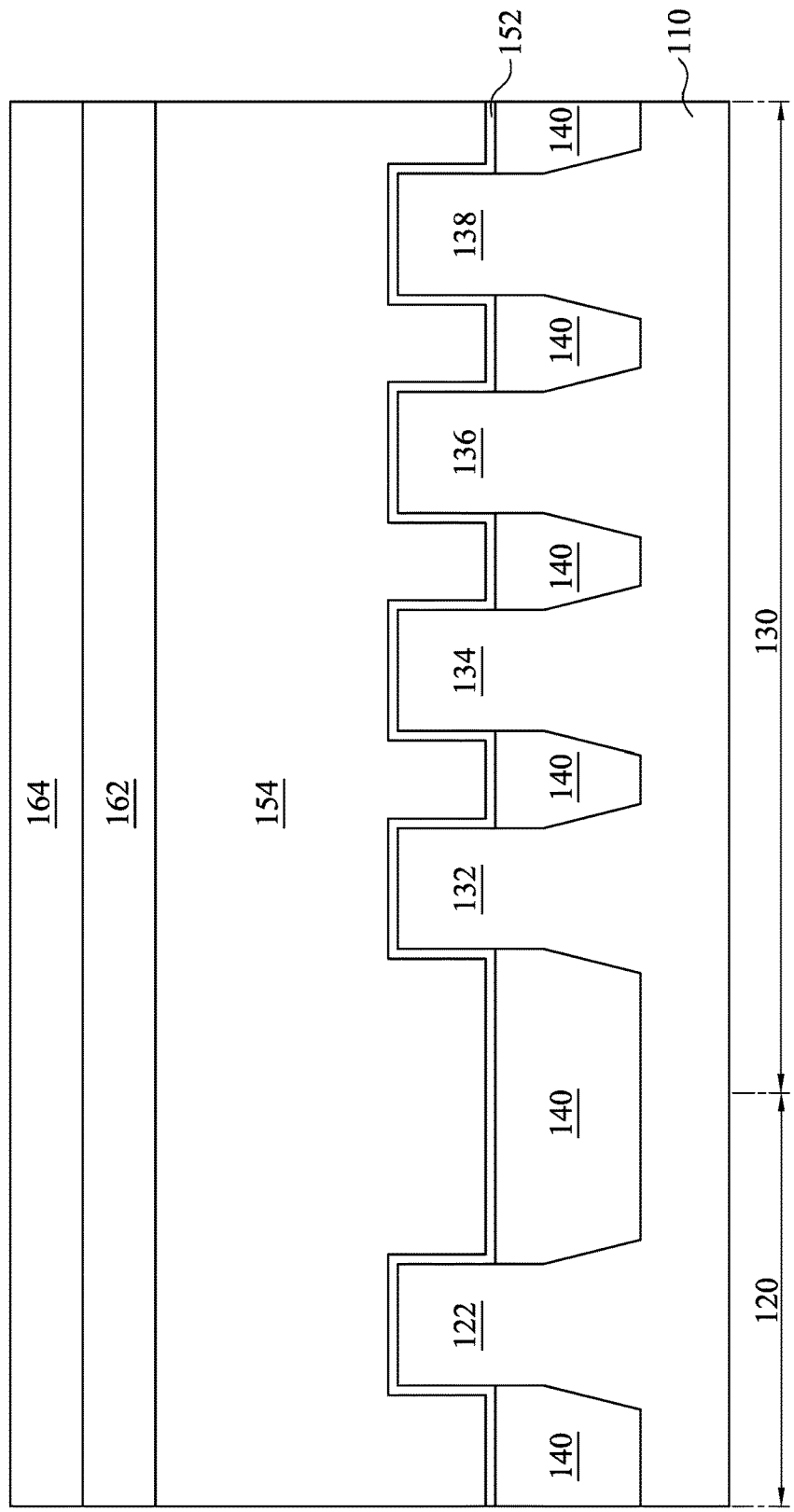

Referring to FIG. 2, a three dimensional view of a FinFET device with a gate structure having two notch features therein is provided first for understanding the present disclosure more easily and clearly. In the following discussions related to a the method 1000 of forming the FinFET device, a plurality of cross sectional views of the FinFET device along line A-A, line B-B, and line C-C are shown in FIG. 3A to FIG. 7A, FIG. 3B to FIG. 7B, and FIG. 6C to FIG. 7C respectively for best understanding the present disclosure.

Referring to FIGS. 1, 2, 3A, and 3B, the method 1000 starts from step 1002 by forming fins 122, 132, 134, 136, and 138 supported by a substrate 110. The substrate 110 comprises two areas: a center area 120 with the fin 122 thereon; and a peripheral area 130 with the fins 132, 134, 136, and 138 thereon. It should be noticed that the center area 120 and the peripheral area 130 may located at either a dense area or an iso area respectively, wherein the dense area is defined to be an area with a high density of fins thereon, while the iso area is defined to be an area with a low density of fins thereon. In other embodiments, the substrate 110 comprises a dense area 130 and an iso area 120. Furthermore, the dense area 130 and the iso area 120 may both located at a center area of the substrate 110 or a peripheral area of the substrate 110.

The substrate 110 may be a bulk silicon substrate. Alternatively, the substrate 100 may comprise an elementary semiconductor, such as silicon (Si) or germanium (Ge) in a crystalline structure; a compound semiconductor, such as silicon germanium (SiGe), silicon carbide (SiC), gallium arsenic (GaAs), gallium phosphide (GaP), indium phosphide (InP), indium arsenide (InAs), and/or indium antimonide (InSb); or a combination thereof. Further, the substrates 110 may also include a silicon-on-insulator (SOI) substrate. Generally, an SOI substrate comprises a layer of a semiconductor material such as silicon (Si), germanium (Ge), silicon germanium (SiGe), silicon germanium on insulator (SGOI), or a combination thereof. The SOI substrate 100 is fabricated using separation by implantation of oxygen (SIMOX), wafer bonding, and/or other suitable methods. Other substrates that may be used include multi-layered substrates, gradient substrates, or hybrid orientation substrates. In the embodiment, the substrate 110 is a bulk silicon substrate. That is to say, fins 122, 132, 134, 136, and 138 are physically connected to the substrate 110.

Still referring to FIGS. 1, 2, 3A, and 3B, the method 1000 proceeds to step 1004 by forming an isolation structure 140 between fins 122, 132, 134, and 138. The isolation structure 140 functions as an insulating layer or an isolation layer for separating two active areas comprising such as epitaxy 200 in the fins 122, 132, 134, and 138. The isolation structure 140 may comprise any suitable insulating materials such as, for example but not limited to, silicon oxide ($SiO_2$), silicon nitride (SiN), silicon oxynitride (SiON), fluoride-doped silicate glass, a low-k dielectric material, and a combination thereof. As used herein, the term "low-k dielectric" refers to the material having a dielectric constant, k, smaller than about 3.9, which is the k value of $SiO_2$. The isolation strcuture 140 may also comprise flowable material such as, for example, silicate, siloxane, methyl SilsesQuioxane (MSQ), hydrogen SisesQuioxane (HSQ), MSQ/HSQ, perhydrosilazane (TCPS), perhy-dro-polysilazane (PSZ), a tetraethyl orthosilicate (TEOS), or a silyl-amine, such as trisilylamine (TSA).

Referring to FIGS. 1, 2, 4A, and 4B, the method 1000 proceeds to step 1006 by depositing a gate oxide layer 152 on the fins and a gate material layer 154 on the gate oxide layer 152. The gate oxide layer 152 may comprise LaO, AlO, ZrO, TiO, $SiO_2$, $Ta_2O_5$, $Y_2O_3$, $SrTiO_3$ (STO), $BaTiO_3$ (BTO), BaZrO, HfZrO, HfLaO, HfSiO, LaSiO, AlSiO, HfTaO, HfTiO, $(Ba,Sr)TiO_3$ (BST), $Al_2O_3$, $Si_3N_4$, oxynitrides (SiON), or other suitable materials. While the gate material layer 154 may comprise a conductive material, such as a metal (e.g., tantalum, titanium, molybdenum, tungsten, platinum, aluminum, hafnium, ruthenium), a metal silicide (e.g., titanium silicide, cobalt silicide, nickel silicide, tantalum silicide), a metal nitride (e.g., titanium nitride, tantalum nitride), doped poly-crystalline silicon, other conductive materials, or a combination thereof. In some embodiments, the gate oxide layer 152 and the gate material layer 154 are formed by a deposition process, such as chemical vapor deposition (CVD).

Referring to FIGS. 1, 2, 5A, and 5B, the method 1000 proceeds to step 1008 by depositing a first hard mask layer 162 on the gate material layer 154 and a second hard mask layer 164 on the first hard mask layer 162. The first hard mask layer 164 and the second hard mask layer may comprises a same material or a different material selected from SiC, SiCN, SiN, TaO, $TiO_2$, $SiO_2$, $Si_3N_4$, SiON, any suitable material, or a combination thereof. In some embodiments, the first hard mask layer 162 and the second hard mask layer 164 are formed by a deposition process, such as chemical vapor deposition (CVD). In other embodiments, the first hard mask layer 162 may comprise a multiple structure. In yet other embodiments, only a hard mask layer such as the first mask layer 162 is formed on the gate material layer 154.

Referring to FIGS. 1, 2, and 6A-6C, the method 1000 proceeds to step 1010 by etching the second hard mask layer 164, the second hard mask layer 162, and the gate material layer 154 to form gate structures 170 and 171 with two notch features therein. Before performing the etching process of step 1006, the first hard mask layer 162 and the second hard mask layer 164 are patterned through a suitable photolithographic process to form a pattern thereon. Followed by an etching process to form the gate structure 170 and 171 as well as a first hard mask 180 and a second hard mask 190 on the gate structure 170 and 171.

The etching process may comprise dry etching, wet etching, plasma etching, reactive-ion etching, a combination thereof, or other suitable processes. The etching gas used in the etching process may comprise HBr, $CF_4$, $CHF_3$, $CH_4$, $CH_2F_2$, $N_2H_2$, $BCl_3$, $Cl_2$, $N_2$, $H_2$, $O_2$, He, Ar, and a combination thereof. To make the gate structure 170 in the center area 120 and the gate structure 171 in the peripheral area 130 both have two notch features with a same profile, some etching parameters needs to be tuned. The etching parameters of a dry plasma etching process may include etching temperature, etching pressure, source power, RF bias voltage, RF bias power, gas flow, over etching time, and other suitable parameters. In the embodiment, the gas flow is not uniform at a center area 120 and a peripheral area 130. In the embodiment, the ratio of the gas flow at the center area to the gas flow at the peripheral area is in a range between about 0.2 to about 1. In some embodiments, the ratio is less than 0.2. That is to say, the gas flow at the peripheral area 130 is larger than that at the center area 120 so that an etching rate of the gate material layer 154 at the peripheral area 130 is as similar as that in the center area 120. It should be noticed that a higher etching rate of the gate material layer 154 at the peripheral area 130 improves an under etching situation in the peripheral area 130 in the traditional etching way (i.e. same gas flow at the peripheral area 130 and at the center area 120) and avoid a footing feature which may cause a short circuit issue from occurring.

Furthermore, other parameters of the dry plasma etching process may improve the etching process of the gate material layer 154. In the embodiment, the etching pressure is in a range between about 13 mtorr and about 20 mtorr. In some embodiments, the etching pressure is higher than about 20 mtorr or lower than about 13 mtorr. In the embodiment, the RF bias voltage is in a range between about 160 V and about 180 V. In some embodiments, the RF bias voltage is higher than about 180 V or less than about 160 V. In the embodiment, the over etching time is in a range between about 30 seconds to about 32 seconds. In some embodiments, the over etching time is longer than about 32 seconds or shorter than 30 seconds. By applying these etching parameters, an under etching situation occurred in the peripheral area 130 in a traditional way may be improved to avoid the footing feature.

In addition, by properly choosing parameters of an etching process, the gate structures 170 and 171 at either a dense area or an iso area of a center area or a peripheral area both have two notch features in a first portion and a second portion of the gate structures 170 and 171 respectively.

Figure 6A:
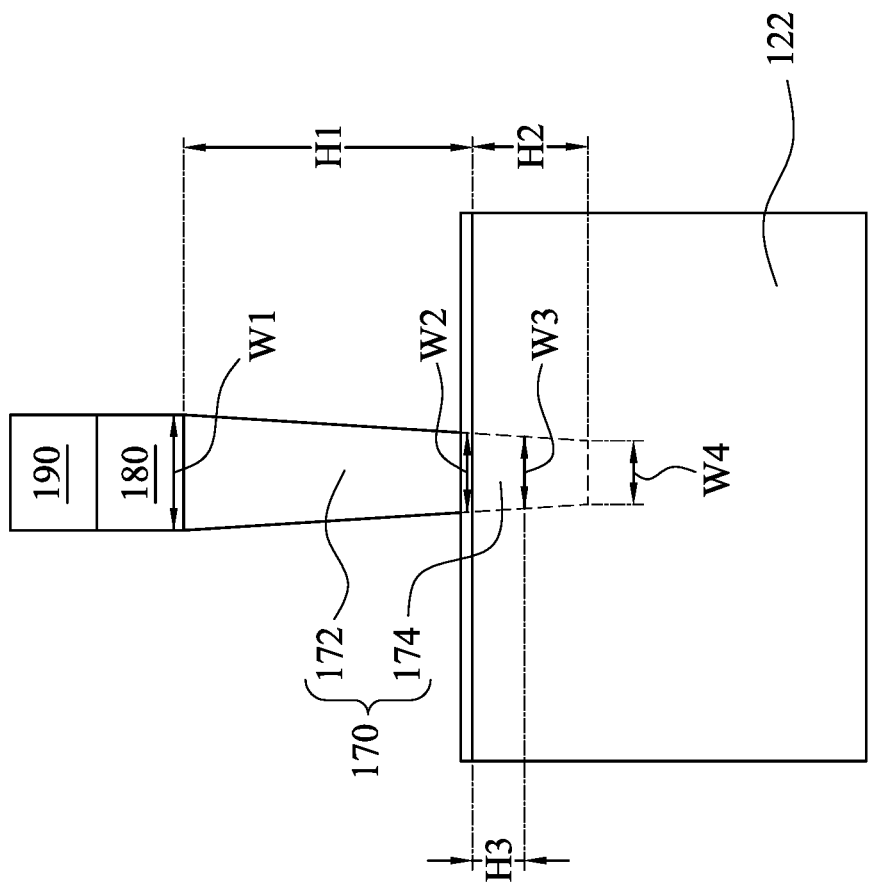
Figure 6B:
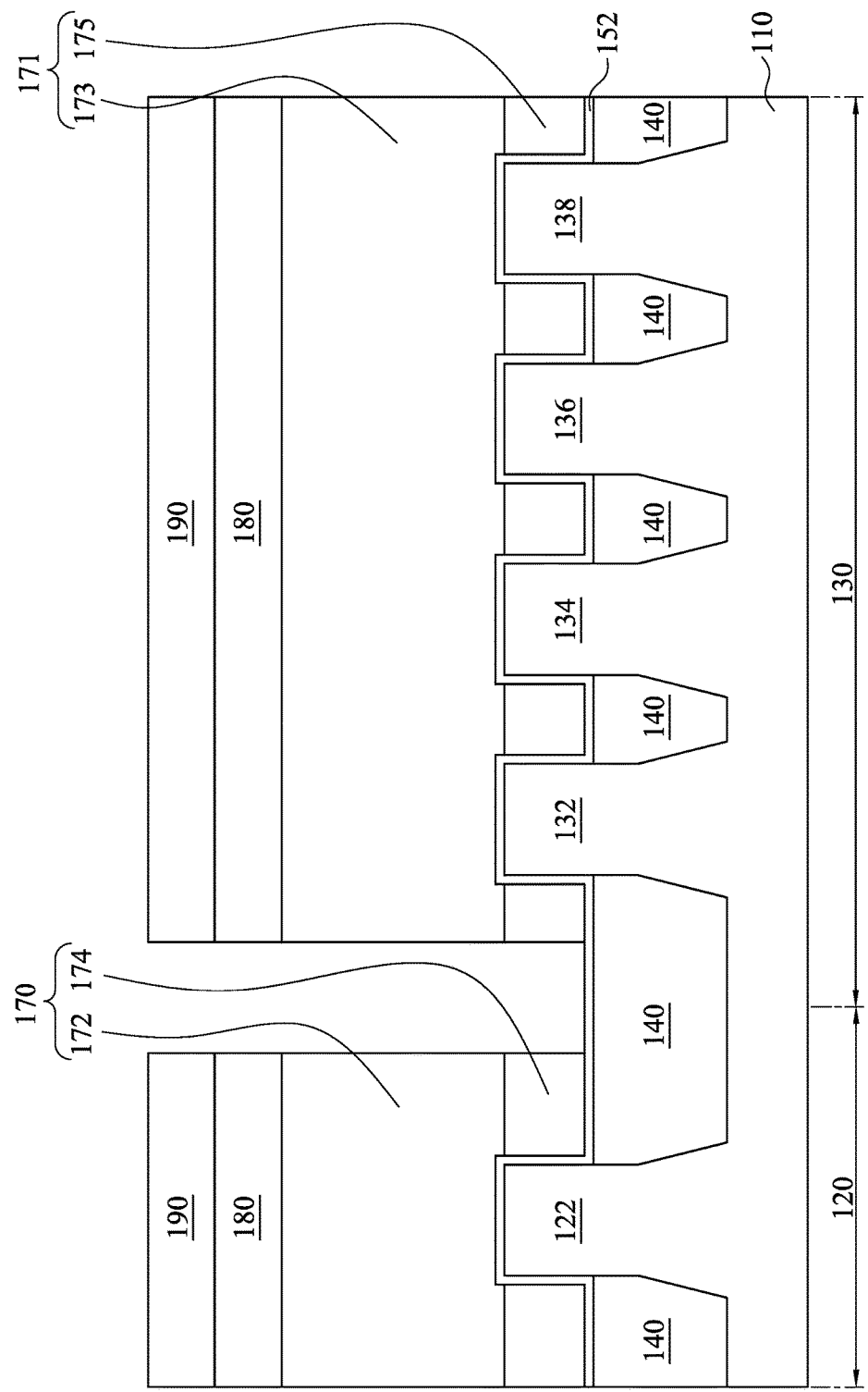

Referring to FIG. 6A, the gate structure 170 in the center area 120 has a first portion 172 over the fin 122 and a second portion 174 overlapped with sidewalls of the fin 122. That is to say, the gate structure 170 is separated into two parts connected to each other. And the bottom surface of the first portion 172 is overlapped with the top surface of the second portion 174. The notch feature in the first portion 172 comprises a set of distances comprising a first width (W1) at a top surface of the first portion 172 and a first height (H1) from a top surface of the first portion 172 to the fin 122. On the other hand, the notch feature in the second portion 174 comprises a set of distances comprising a second width (W2) at a top surface of the second portion 174, a third width (W3) at a middle position of the second portion 174, a fourth width (W4) at a bottom surface of the second portion 174, a second height (H2) from a bottom surface of the second portion 174 to the fin 122, and a third height (H3) form a middle position of the second portion 174 to the fin 122. It should be noticed that each of the set of distances mentioned above is referenced to the second width (W2), and a relative position between any two of the set of the distances can be calculated and known by the aforementioned definitions of the set of distances.

Figure 6C:
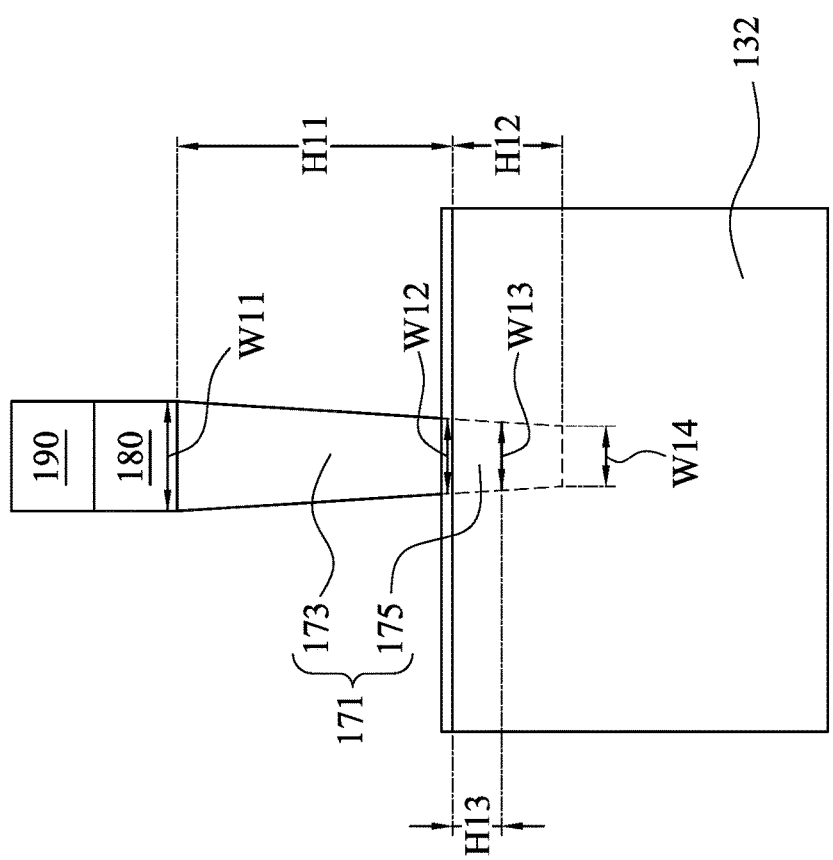
FIGS. 6C and 7C illustrate various cross sectional views of a FinFET device along line C-C in FIG. 2 at different stages of manufacturing processes in accordance with the embodiments.

Referring to FIG. 6C, the gate structure 171 in the peripheral area 130 has a first portion 173 over the fin 132 and a second portion 175 overlapped with sidewalls of the fin 132. That is to say, the gate structure 171 is separated into two parts connected to each other. And the bottom surface of the first portion 173 is overlapped with the top surface of the second portion 175. The notch feature in the first portion 173 comprises a set of distances comprising first width (W11) at a top surface of the first portion 173 and a first height (H11) from a top surface of the first portion 173 to the fin 132. On the other hand, the notch feature in the second portion 175 comprises a set of distances comprising a second width (W12) at a top surface of the second portion 175, a third width (W13) at a middle position of the second portion 175, a fourth width (W14) at a bottom surface of the second portion 175, a second height (H12) from a bottom surface of the second portion 175 to the fin 132, and a third height (H13) form a middle position of the second portion 175 to the fin 132.

In the embodiment, the gate structure 170 and the gate structure 171 have the notch features with the same profile (or the same set of distances) in the first portion 172 and 173 and in the second portion 174 and 175 respectively. Furthermore, the set of distances of the notch features of the gate structures 170 and 171 mentioned above may be used in a comparison with a predetermined criterion for obtaining a quality related to electric properties of the FinFET device, which will be discussed later.

Figure 7A:
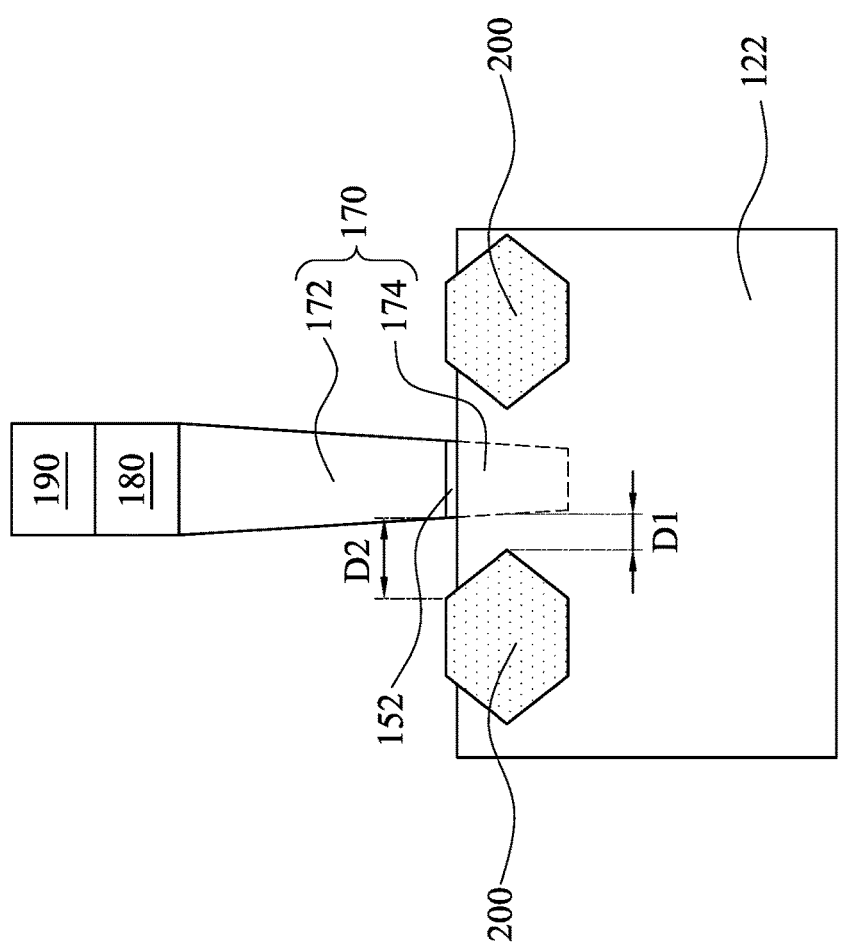
Figure 7B:
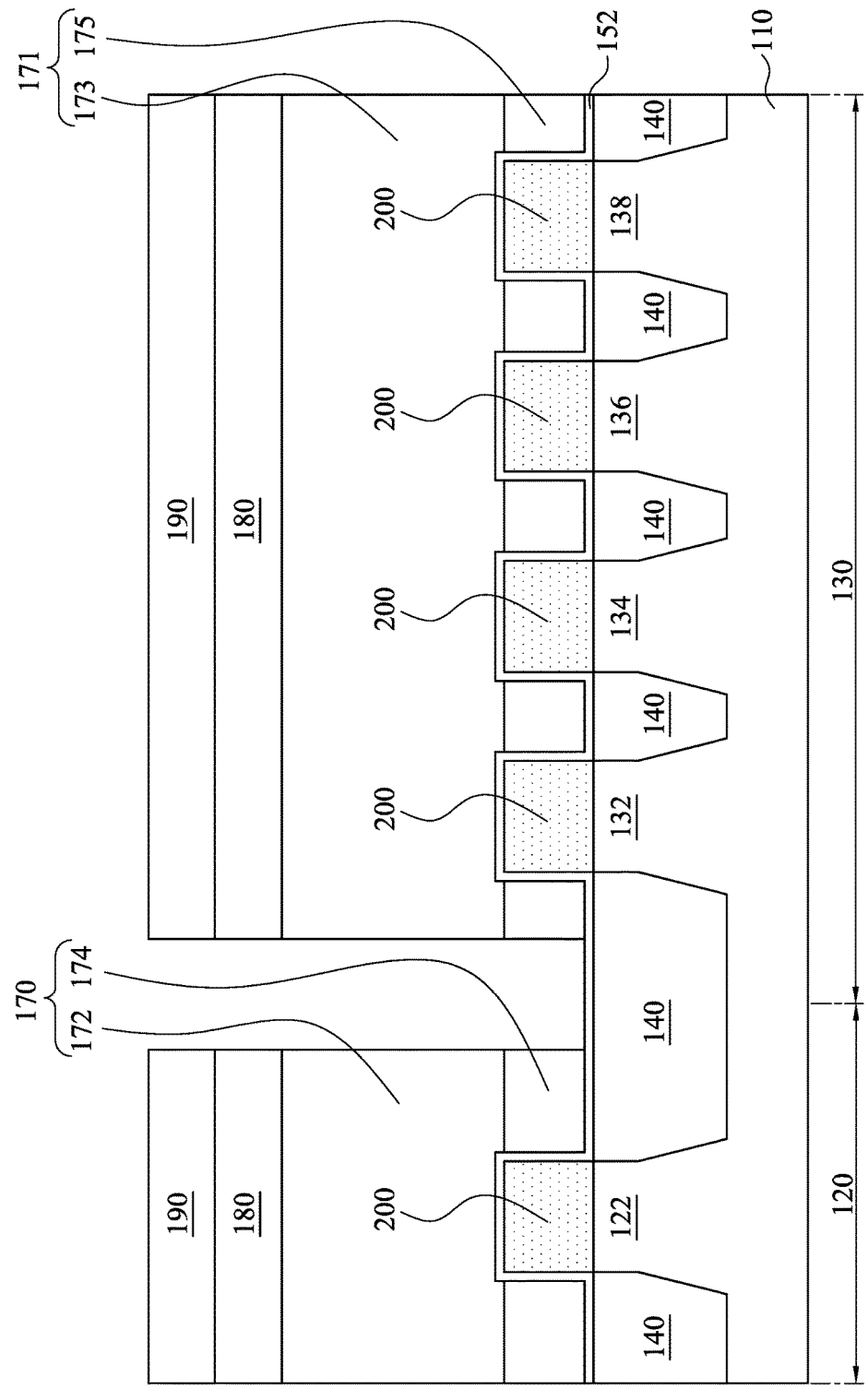
Figure 7C:
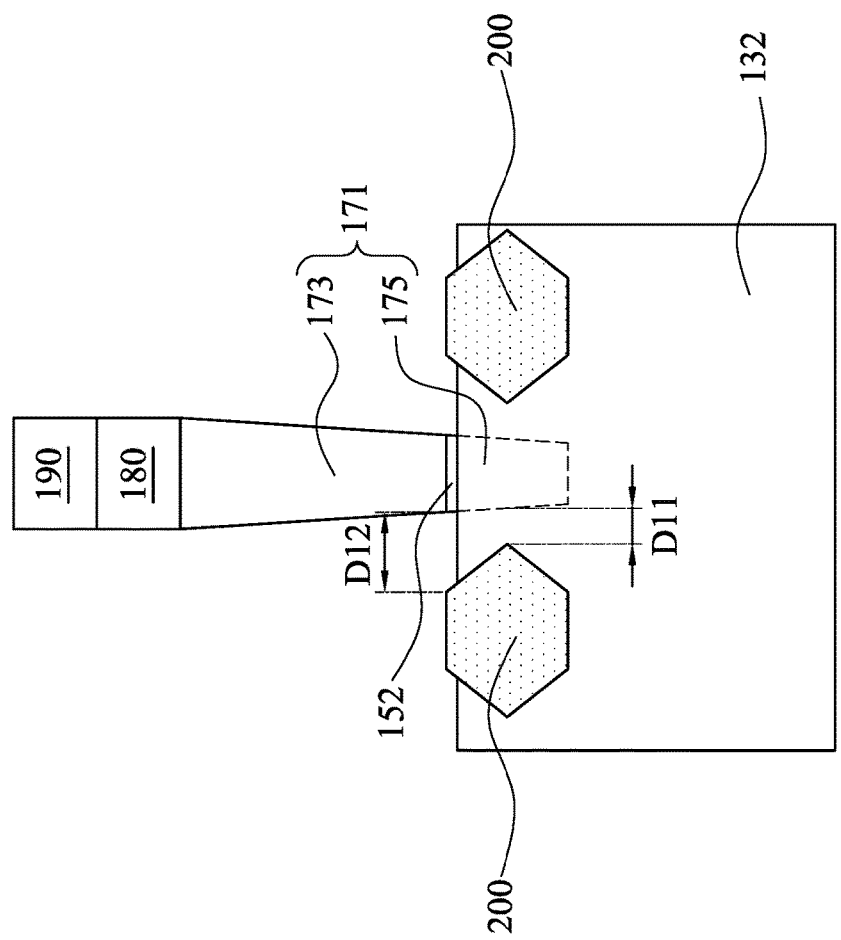

Referring to FIGS. 1, 2, and 7A-7C, the method 1000 proceeds to step 1012 by forming epitaxy 200 in the fins 122 and 132 respectively. The epitaxy 200 may be formed by depositing a crystalline in a recess (not shown) of the fins 122 and 132. As shown in FIG. 7A, there is a distance D1 between the epitaxy 200 and the second portion 174 of the gate structure 170, and a distance D2 between the epitaxy 200 and the first portion 172 of the gate structure 170. On the other hand, as shown in FIG. 7C, there is a distance D11 between the epitaxy 200 and the second portion 175 of the gate structure 171, and a distance D12 between the epitaxy 200 and the first portion 173 of the gate structure 171. The distance D1, D2, D11 and D12 should be precisely controlled to avoid short circuit from occurring. In the embodiment, the notch feature in the second portion 174 and 175 of the gate structure 170 and 171 may provide a larger distance D1 and D11 so that a process window may be enlarged and a stability of a semiconductor device may be increased. Furthermore, the notch feature in the first portion 172 and 173 of the gate structure 170 and 171 may also provide a larger distance D2 and D12, thus a short circuit issue caused by a footing feature may be avoided as well.

Figure 8:
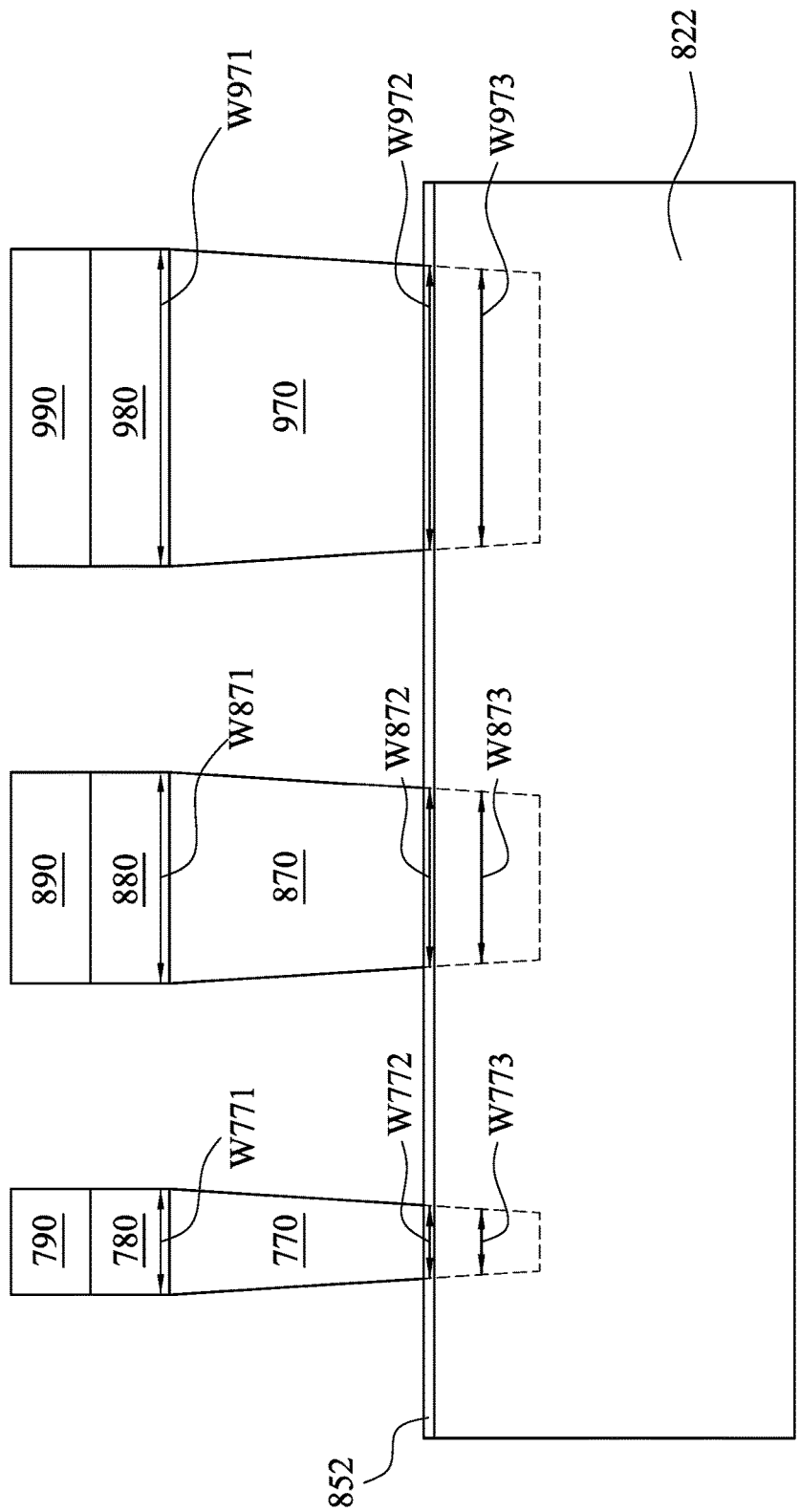
FIG. 8 illustrate a cross sectional views of a FinFET device in accordance with the embodiments.

In other embodiments as shown in FIG. 8, gate structures may comprise different width, thus different channel lengths may be formed under gate structures for design requirements. As shown in FIG. 8, gate structures comprising a short channel gate 770, a middle channel gate 870, and a long channel gate 970 are formed on a fin 822 and a gate oxide layer 852. In addition, each gate structure 770, 870, and 970 comprises a first hard mask 780, 880, and 980 and a second hard mask 790, 890, and 990 respectively. By using the etching method with particular etching parameters mentioned above, the short channel gate 770, the middle channel gate 870, and the long channel gate 970 can have two notch features with a same profile therein. To be more precisely, a difference between each one of the set of distance of the notch features mentioned above in FIG. 6 is the same among the short channel gate 770, the middle channel gate 870, and the long channel gate 970. For example, a difference between a first width (W771) and a second width (W772) of the short channel gate 770 is equal to a difference between a first width (W871) and a second width (W872) of the middle channel gate 870. And a difference between a second width (W772) and a third width (W773) of the short channel gate 770 is equal to a difference between a second width (W872) and a third width (W873) of the middle channel gate 870. Also, a difference between a second width (W872) and a third width (W873) of the middle channel gate 870 is equal to a difference between a second width (W972) and a third width (W973) of the long channel gate 970. And a difference between a first width (W871) and a second width (W872) of the middle channel gate 870 is equal to a difference between a first width (W971) and a second width (W972) of the long channel gate 970. Thus, the etching method with particular parameters mentioned above can be used to form the same difference between any two distances of the set of distances when comparing gate structures with different gate width.

Figure 9:
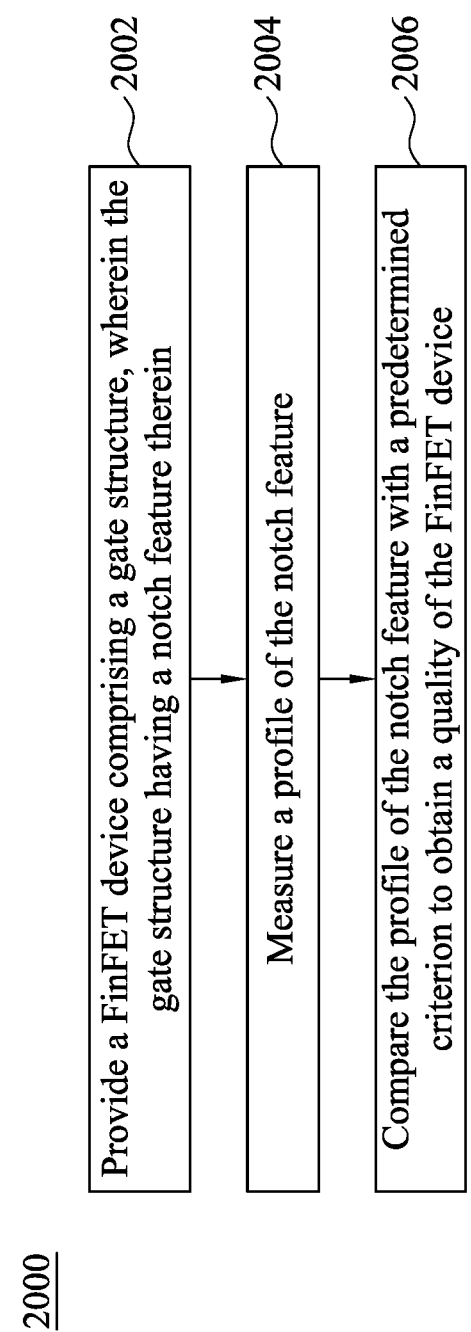
FIG. 9 illustrates an exemplary flow chart of monitoring a quality of a FinFET device in accordance with the embodiments.

Now referring to FIG. 9, which is an exemplary flow chart of monitoring a quality of a FinFET device according to one embodiment of the present disclosure. The flow chart illustrates only a relevant part of the entire manufacturing process. It is understood that additional operations may be provided before, during, and after the operations shown by FIG. 9, and some of the operations described below can be replaced or eliminated for additional embodiments of the method. The order of the operations/processes may be interchangeable.

Referring to FIG. 9, the method 2000 of monitoring a quality of a FinFET device starts from step 2002 by providing a FinFET device comprising a gate structure having a notch feature therein. The FinFET device may be provided by the manufacturing method 1000 mentioned above in FIG. 1. Alternatively, the FinFET device may be received from other embodiments. The method 2000 discussed herein only refers to a monitoring method regardless of a source of the FinFET device.

Referring to FIG. 9, the method 2000 proceeds to step 2004 by measuring a profile of the notch feature in the gate structure. The method of measuring the profile of the notch feature may be an inline inspection. The measuring method may use a TEM method comprising slicing the substrate including the notch feature and then performing an electron microscope scanning to measure the profile of the notch feature. By observing a cross sectional TEM image of the notch feature, each distance of the set of distances mentioned above in FIG. 6 can be obtained directly and precisely. Alternatively, the measuring method may use an optical critical-dimension (OCD) inspection. The OCD measuring method comprises irradiating a notch feature with an incident electromagnetic wave, receiving an emitted electromagnetic wave from the notch feature after an interaction between the incident electromagnetic wave and the notch feature, and obtaining the profile of the notch feature by calculating a polarization change between the incident electromagnetic wave and the emitted electromagnetic wave. The OCD inspection can be used to provide a non-destructive measurement for obtaining the distance of the set of distances mentioned above.

Referring to FIG. 9, the method 2000 proceeds to step 2006 by comparing the profile of the notch feature with a predetermined criterion for obtaining a quality of the FinFET device. After the profile and each distance of a set of distances mentioned above in FIG. 6A are obtained by the method discussed in the step 2004, the distance of a set of distances of the notch feature is compared with a predetermined criterion. It should be noticed that each distance of a set of distance of the notch feature in FIG. 6A is used for easily and clearly understanding the predetermined criterion. The predetermined criterion comprise following conditions: the first width (W1) is larger than the second width (W2); the second width (W2) is larger than the third width (W3), wherein the difference between the second width (W2) and the third width (W3) is in a range between about 0.001 nm and about 15 nm; and the first height (H1) is larger than the second height (H2), wherein the second height (H2) is in a range between about 0.001 nm and about 50 nm. Since the third width (H3) is half of the second height (H2), the third width (H3) is in a range between about 0.001 nm and about 25 nm. It should be noticed that the fourth width (W4) is not limited in the predetermined criterion, thus a width of the fourth width (W4) may be larger than the third width (W3) or smaller than the third width (W3). In the embodiment, the second portion 174 comprises smooth sidewalls with a same slope so that the fourth width (W4) is smaller than the third width (W3). It should be noticed that the criterion is applied to the notch feature of all gate structures in a FinFET device. It should be noticed that a half upper part of the second portion 174 having a specific profile, comprising a second width (W2), a third width (W3), and a third height (H3) as shown in FIG. 6A. Further, the second portion 174 has a slope on a sidewall thereof. The slope is defined as ratio of the third height (H3) to the difference between the second width (W2) and the third width (W3), and a positive slope represents a slope of the second portion 174 having a second width (W2) larger than the third width (W3), while a negative slope represents a slope of the second portion 174 having a second width (W2) smaller than the third width (W3). In the embodiment, the slope is in a range between 0.000067 and 25000. In some embodiments, the slope is in a range between 0.067 and 25. By controlling the slope of the second portion 174 of the gate structure 170, the gate structure 170 will operate normally and pass a WAT (wafer acceptance test).

Furthermore, once the distance of a set of distances of the notch feature meets the predetermined criterion mentioned above, items of a subsequent wafer acceptance test (WAT) also meet a predetermined standard value, thus proving that electrical properties and stability of a FinFET device is good or acceptable. The items of a WAT related to a gate structure may comprise Rc, Cgd, Cgg, Rg, drain-induced barrier lowering (DIBL), and other test items.

As aforementioned, a method of forming gate structures having two notch features with a same profile is very important for improving electrical performance and stability of a semiconductor device. It is known that during a traditional way to etch a gate material layer to form gate structures may result in an uncontrollable dimension in gate structures locating in different zones (i.e. center/peripheral areas or dense/iso areas) of a substrate. The uncontrollable dimension of gate structure may lead to defects, such as short circuit caused by a footing feature of a gate structure, in some under-etched gate structures. Hence, a method is needed for improving dimension controlling of gate structures so as to prevent short circuit from occurring.

A method disclosed according to the embodiments to dissolve the problem described above of the dimension controlling of gate structures during an etching process of a gate material layer is providing a different gas flow at a center area and at a peripheral area of a substrate and tuning etching parameters such as etching pressure, bias power, and over etching time. By properly tuning a gas flow and other etching parameters, all formed gate structures have two notch features with a same profile. Furthermore, gate structures with different gate width also have two notch features with a same difference between each distance of a set of distances of the notch feature. In addition, the set of distances of the notch feature are correlated to wafer acceptance test (WAT) items. In other words, the set of distance of the notch features may provide information for determining a quality of a FinFET device. That is to say, once the distances of the set of distances of the notch feature meet a predetermined criterion, the related outcome WAT result will be good and acceptable. In summary, the method in the disclosure can form two notch features with a same profile in all gate structures. And the profile (or the set of distances) of the notch features all meet a predetermined criterion to have a good quality of a FinFET device.

In accordance with some embodiments of the present disclosure, a method of forming a FinFET structure, the method comprises: forming a plurality of fins supported by a substrate; depositing a gate layer on the fins; and etching the gate layer by plasma etching with an etching gas to form a gate having two notch features in a first portion over the fin and in a second portion overlapped with sidewalls of the fin. The substrate has a center area and a peripheral area. The etching gas during the plasma etching is supplied at a ratio of a flow rate at the center area to a flow rate at the periphery area in a range from 0.2 to 1.

In accordance with some embodiments of the present disclosure, a method of monitoring a quality of a FinFET device, the method comprising: providing the FinFET device comprising a fin supported by a substrate and a gate structure having a notch feature in a portion overlapped with sidewalls of the fin; measuring a profile of the notch feature; and obtaining the quality of the FinFET device by comparing the profile of the notch feature with a predetermined criterion.

In accordance with some embodiments of the present disclosure, a FinFET device comprises a substrate, a fin supported by the substrate, and a gate structure having two notch features. The two notch features are in a first portion over the fin and a second portion overlapped with sidewalls of the fin. A profile of the notch features comprises: a first width at a top surface of the first portion; a second width at a top surface of the second portion; a third width at a middle position of the second portion; a fourth width at a bottom surface of the second portion; a first height from the first width to the second width; a second height from the second width to the third width; and a third height from the third width to the fourth width. Wherein the third width is smaller than the second width and a difference between the third width and the second width is in a range between 0.001 nm and 25 nm; and the second height is in a range between 0.001 nm and 25 nm The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of forming a FinFET device, the method comprising:
    forming a plurality of fins supported by a substrate having a center area and a periphery area;
    depositing a gate layer on the fins; and
    plasma etching the gate layer with an etching gas to form a first gate having two notch features in a first portion over a first fin and in a second portion overlapped with sidewalls of the first fin, wherein the etching gas is applied at a ratio in a range from 0.2 to 1 of a flow rate at the center area to a flow rate at the periphery area.

2. The method of claim 1, wherein the plasma etching is performed by applying the etching gas in a pressure ranging from 13 mtorr to 20 mtorr.

3. The method of claim 1, wherein the plasma etching is performed by applying a RF bias voltage in a range from 160 V to 180 V.

4. The method of claim 1, wherein the plasma etching is performed by applying an over etching time in a range from 30 s to 32 s.

5. The method of claim 1, wherein the etching gas is selected from a group consisting of HBr, $CF_4$, $CHF_3$, $CH_4$, $CH_2F_2$, $N_2H_2$, $BCl_3$, $Cl_2$, $N_2$, $H_2$, $O_2$, He, Ar and a combination thereof.

6. The method of claim 1, wherein the first fin is in the center area, the method comprising:
    plasma etching the gate layer with an etching gas to also form a second gate having two notch features in a first portion over a second fin and in a second portion overlapped with sidewalls of the second fin, wherein the two notch features in the first portion over the second fin and the second portion overlapped with sidewalls of the second fin have a same profile as the two notch features in the first portion over the first fin and in the second portion overlapped with sidewalls of the first fin.

7. The method of claim 6, wherein the plurality of fins has a first fin density in the center area and the plurality of fins has a second fin density greater than the first fin density in the peripheral area.

8. The method of claim 6, wherein the first portion of the first gate has a first width when measured in a direction parallel to a main axis of the first fin and the first portion of the second gate has a second width when measured in a direction parallel to a main axis of the second fin, the second width being greater than the first width.

9. The method of claim 8, wherein the second portion of the first gate has a third width when measured in a direction parallel to a main axis of the first fin and the second portion of the second gate has a fourth width when measured in a direction parallel to a main axis of the second fin, and wherein a ratio of the first width to the third width is the same as a ratio of the second width to the fourth width.

10. A method of monitoring a quality of a FinFET device, the method comprising:
    providing the FinFET device comprising a fin supported by a substrate; and a gate structure having a notch feature in a portion overlapped with sidewalls of the fin;
    measuring a profile of the notch feature by measuring respective outermost widths of the gate structure at respective location of the gate structure, the respective locations being at different heights of the gate structure above substrate; and
    obtaining the quality of the FinFET device by comparing the profile of the notch feature with a predetermined criterion.

11. The method of claim 10, wherein measuring the profile of the notch feature, comprises:
    slicing the FinFET device including the notch feature; and
    performing an electron microscope scanning to obtain the profile of the notch feature.

12. The method of claim 10, wherein measuring the profile of the notch feature, comprises:

irradiating the notch feature with an incident electromagnetic wave;
receiving an emitted electromagnetic wave from the notch feature after an interaction between the incident electromagnetic wave and the notch feature; and
obtaining the profile of the notch feature by calculating a polarization change between the incident electromagnetic wave and the emitted electromagnetic wave.

13. The method of claim 10, wherein measuring the profile of the notch feature is measuring a set of distances comprising:
a first width at a top surface of the portion;
a second width at a middle position of the portion; and
a first height from the first width to the second width.

14. The method of claim 13, wherein obtaining the quality of the FinFET device is comparing the profile of the notch feature with a predetermined criterion comprising:
the first width is larger than the second width, wherein a difference between the first width and the second width is in a range between 0.001 nm to 15 nm; and
the first height is in a range between 0.001 nm to 25 nm.

15. A method of forming a FinFET device, the method comprising:
forming a plurality of fins extending from a semiconductor layer, the plurality of fins having a first fin density in a center area of the semiconductor layer and a second fin density different than the first fin density in a periphery area of the semiconductor layer;
depositing a gate layer on the plurality of fins; and
etching the gate layer with form respective first gates over respective fins in the center area and respective second gates over respective fins in the periphery area, by subjecting the gate layer to an etching gas at a first flow rate in the center area simultaneously with subjecting the gate layer to the etching gas at a second flow rate in the periphery area.

16. The method of claim 15, wherein a ratio of the first flow rate to the second flow rate is from about 0.2 to about 1.

17. The method of claim 15, wherein the respective first gates have respective first top widths and respective first bottom widths, the respective second gates have respective second top widths and respective second bottom widths, and a ratio of the respective first top widths to the respective first bottom widths is the same as a ratio of the respective second top widths to the respective second bottom widths.

18. The method of claim 17, wherein the respective first bottom widths are greater than the respective first top widths.

19. The method of claim 15, wherein the second fin density is greater than the first fin density.

20. The method of claim 15, further comprising:
determining a profile of respective sidewalls of at least one first gate and at least one second gate; and
making a determination of the quality of the FinFET device by comparing the profile of the respective sidewalls with a predetermined criterion.

* * * * *